(12) United States Patent
Kobayashi

(10) Patent No.: US 11,185,673 B2
(45) Date of Patent: Nov. 30, 2021

(54) MICRO-NEEDLE ARRAY UNIT AND CONTAINER

(71) Applicant: FUJIFILM Corporation, Tokyo (JP)

(72) Inventor: Yuka Kobayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 241 days.

(21) Appl. No.: 15/979,412

(22) Filed: May 14, 2018

(65) Prior Publication Data
US 2018/0326193 A1    Nov. 15, 2018

(30) Foreign Application Priority Data
May 15, 2017  (JP) .............................. JP2017-096640

(51) Int. Cl.
*A61M 5/00* (2006.01)
*A61M 37/00* (2006.01)

(52) U.S. Cl.
CPC . *A61M 37/0015* (2013.01); *A61M 2037/0023* (2013.01); *A61M 2037/0046* (2013.01); *A61M 2209/06* (2013.01)

(58) Field of Classification Search
CPC ...... A61M 37/0015; A61M 2037/0023; A61M 2037/0046; A61M 2209/06; A61M 2037/0061; A61M 2209/00; A61K 9/0021
See application file for complete search history.

(56) References Cited

U.S. PATENT DOCUMENTS

| 6,562,014 B2* | 5/2003 | Lin ................... A61B 5/150984 |
| | | 604/317 |
| 7,097,631 B2* | 8/2006 | Trautman ............. A61B 17/205 |
| | | 604/22 |

(Continued)

FOREIGN PATENT DOCUMENTS

| CN | 102553064 | 7/2012 |
| CN | 105916543 | 8/2016 |

(Continued)

OTHER PUBLICATIONS

"Search Report of European Counterpart Application," dated Oct. 15, 2018, p. 1-p. 10.

(Continued)

*Primary Examiner* — Rebecca E Eisenberg
(74) *Attorney, Agent, or Firm* — JCIPRNET

(57) ABSTRACT

A micro-needle array unit includes a micro-needle array; a container which accommodates the micro-needle array and includes an accommodating portion having an opening and a protrusion that supports the outer peripheral surface of the micro-needle array, a deformation portion disposed on a side opposite to the opening and integrated with the accommodating portion, and a flange portion integrated with the accommodating portion and brought into contact with the skin; and a lid which seals the opening of the container, in which the deformation portion is deformed and the other surface of the micro-needle array is pressed due to an external force being applied in a direction of the opening, the micro-needle array deforms the protrusions and is pushed to the outside from the accommodating portion by the pressing of the other surface of the micro-needle array, and the deformation portion maintains the deformed state and presses the micro-needle array.

12 Claims, 9 Drawing Sheets

(56) References Cited

U.S. PATENT DOCUMENTS

| | | |
|---|---|---|
| 8,267,889 B2 | 9/2012 | Cantor et al. |
| 8,758,298 B2 | 6/2014 | Cantor et al. |
| 8,821,446 B2 | 9/2014 | Trautman et al. |
| 10,035,008 B2 | 7/2018 | Brandwein et al. |
| 10,525,243 B2 | 1/2020 | Kato |
| 2008/0183144 A1 | 7/2008 | Trautman et al. |
| 2008/0195035 A1* | 8/2008 | Frederickson .... A61M 37/0015 604/22 |
| 2009/0198189 A1* | 8/2009 | Simons .............. A61M 37/0015 604/173 |
| 2012/0078189 A1 | 3/2012 | Ogawa et al. |
| 2012/0143119 A1* | 6/2012 | Deasey .............. A61M 37/0015 604/20 |
| 2012/0277697 A1* | 11/2012 | Haghgooie .......... A61B 5/1411 604/319 |
| 2015/0196746 A1 | 7/2015 | Ogawa et al. |
| 2015/0290444 A1 | 10/2015 | Wirtanen et al. |
| 2016/0121092 A1* | 5/2016 | Kato ................. A61M 37/0015 604/173 |
| 2016/0213908 A1 | 7/2016 | McAllister et al. |
| 2016/0325081 A1* | 11/2016 | Kato ................. A61M 37/0015 |
| 2016/0325082 A1* | 11/2016 | Kato ................. A61M 37/0015 |
| 2016/0354589 A1* | 12/2016 | Kobayashi ........ A61M 37/0015 |

FOREIGN PATENT DOCUMENTS

| | | | |
|---|---|---|---|
| EP | 3097942 | 11/2016 | |
| JP | 2008520369 | 6/2008 | |
| JP | 2008535587 | 9/2008 | |
| JP | 2010516337 | 5/2010 | |
| JP | 2013226427 | * 11/2013 | ........ A61M 37/0015 |
| JP | 5553612 | 7/2014 | |
| WO | 2008091602 | 7/2008 | |
| WO | 2009107806 | 9/2009 | |

OTHER PUBLICATIONS

"Office Action of Japan Counterpart Application", dated Aug. 3, 2020, with English translation thereof, pp. 1-6.

"Office Action of China Counterpart Application", dated Apr. 25, 2021, with English translation thereof, p. 1-p. 18.

"Office Action of Japan Counterpart Application" with English translation thereof, dated Mar. 23, 2021, p. 1-p. 6.

* cited by examiner

MICRO-NEEDLE ARRAY UNIT AND CONTAINER

CROSS-REFERENCE TO RELATED APPLICATIONS

The present application claims priority under 35 U.S.C. § 119 to Japanese Patent Application No. 2017-096640, filed on May 15, 2017. The above application is hereby expressly incorporated by reference, in its entirety, into the present application.

BACKGROUND OF THE INVENTION

1. Field of the Invention

The present invention relates to a micro-needle array unit and a container.

2. Description of the Related Art

In recent years, a micro-needle array has been known as a new dosage form which enables administration of a medicine into the skin without pain. The micro-needle array is formed by arranging biodegradable micro-needles (also referred to as fine needles) containing a medicine in an array. By pressing this micro-needle array onto the skin, each micro-needle is punctured into the skin. The punctured micro-needles are absorbed by the skin and the medicine contained in each micro-needle is administered into the skin.

A container (also referred to as an applicator) that presses a micro-needle array onto the skin in a state of accommodating the micro-needle array in order to protect micro-needles until the micro-needles are punctured into the skin and to easily puncture the micro-needles into the skin has been suggested (JP5553612B).

SUMMARY OF THE INVENTION

In the container of JP5553612B, an outer portion integrated with an inner portion that holds the micro-needle array is elastically deformed. Accordingly, there is a concern that the size of the container is increased.

The present invention has been made in consideration of the above-described circumstances, and an object thereof is to provide a micro-needle array unit and a container which can be miniaturized.

According to a first aspect, there is provided a micro-needle array unit comprising: a micro-needle array which includes a sheet and a plurality of needles arranged inside an outer peripheral surface of one surface of the sheet; a container which accommodates the micro-needle array and includes an accommodating portion having an opening and a protrusion that supports the outer peripheral surface of the micro-needle array, a deformation portion disposed on a side opposite to the opening and integrated with the accommodating portion, and a flange portion integrated with the accommodating portion and brought into contact with the skin; and a lid which seals the opening of the container, in which the deformation portion is deformed and the other surface of the micro-needle array is pressed due to an external force being applied in a direction of the opening, the micro-needle array passes through the protrusion and is pushed to the outside from the accommodating portion by the pressing of the other surface of the micro-needle array, and the deformation portion maintains the deformed state and presses the micro-needle array.

According to a second aspect of the micro-needle array unit, the protrusion is arranged closer to a side of the opening than a side of the deformation portion.

According to a third aspect of the micro-needle array unit, the deformation portion has a convex shape with a vertex portion separated from the micro-needle array.

According to a fourth aspect of the micro-needle array unit, the convex shape is a dome shape or a cone shape.

According to a fifth aspect of the micro-needle array unit, the protrusions are formed such that a plurality of protrusions are arranged at equal intervals in the accommodating portion.

According to a sixth aspect of the micro-needle array unit, the protrusions are continuously arranged in the accommodating portion.

According to a seventh aspect of the micro-needle array unit, the flange portion includes an adhesive on a side in contact with the skin.

According to an eighth aspect, the micro-needle array unit further comprises a flat plate on a side of the other surface of the micro-needle array.

According to a ninth aspect of the micro-needle array unit, the flange portion is provided in the entire circumference of the accommodating portion.

According to a tenth aspect of the micro-needle array unit, the flange portion includes a bent portion which is bent to the side of the deformation portion.

According to an eleventh aspect of the micro-needle array unit, the bent flange portion is disposed at a position beyond the deformation portion with respect to the opening of the accommodating portion.

According to a twelfth aspect, there is provided a container which accommodates a micro-needle array including a sheet and a plurality of needles arranged inside an outer peripheral surface of one surface of the sheet, the container comprising: an accommodating portion which includes an opening and a protrusion that supports the outer peripheral surface by directing the needles to the opening; a deformation portion which is disposed on a side opposite to the opening and integrated with the accommodating portion; and a flange portion integrated with the accommodating portion and brought into contact with the skin, in which the deformation portion is deformed and the other surface of the micro-needle array is pressed due to an external force being applied in a direction of the opening, and the deformation portion maintains the deformed state and presses the micro-needle array pushed out from the accommodating portion.

According to the present invention, it is possible to miniaturize the micro-needle array unit and the container.

DESCRIPTION OF THE PREFERRED EMBODIMENTS

Hereinafter, preferred embodiments of the present invention will be described with reference to the accompanying drawings. The present invention will be described based on the following preferred embodiments. Modifications can be made according to various techniques without departing from the scope of the present invention and other embodiments other than the embodiments can be used. Therefore, all modifications within the scope of the present invention are included in the scope of the appended claims.

A micro-needle array unit according to an embodiment includes a micro-needle array; a container which allows protrusions to support the micro-needle array; and a lid which seals an opening of the container, in which a portion of the container is deformed by applying an external force from a side opposite to the opening so that the micro-needle array is pushed out from the container and pressed by the deformed container. Hereinafter, preferred embodiments will be described.

Figure 1:
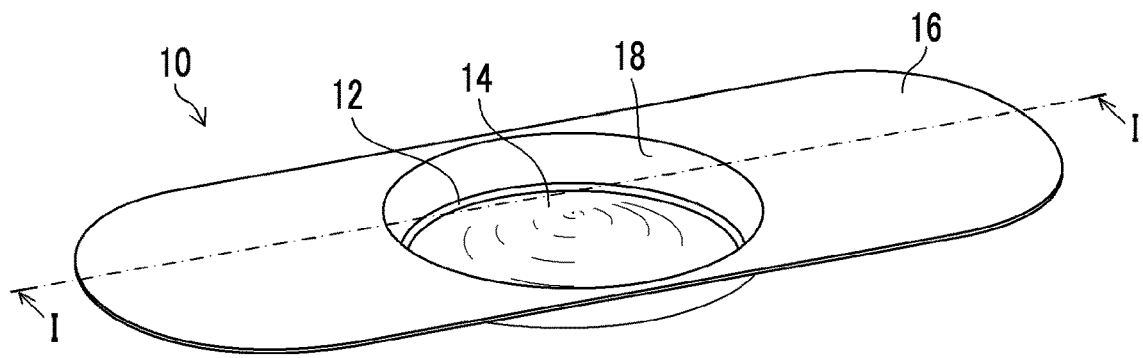
FIG. 1 is a perspective view illustrating a micro-needle array unit.
Figure 2:
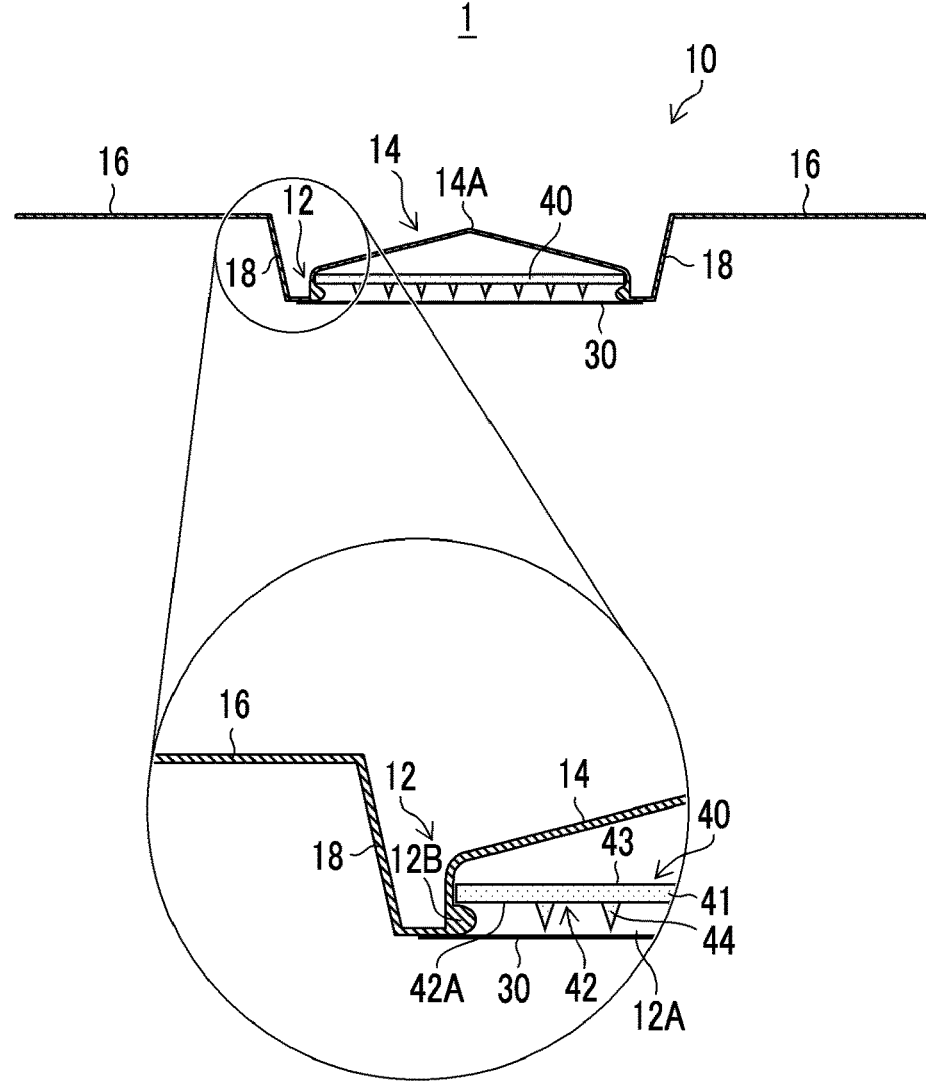
FIG. 2 is a cross-sectional view of the micro-needle array unit taken along line I-I of FIG. 1.

FIG. 1 is a perspective view illustrating a micro-needle array unit. FIG. 2 is a cross-sectional view of the micro-needle array unit taken along line I-I of FIG. 1. A micro-needle array unit 1 will be described based on FIGS. 1 and 2.

As illustrated in FIG. 1, the micro-needle array unit 1 includes a container 10. The container 10 includes: an accommodating portion 12 for accommodating a micro-needle array; a deformation portion 14 integrated with the accommodating portion 12; and a flange portion 16 integrated with the accommodating portion 12 and bent by a bent portion 18.

The accommodating portion 12 and the deformation portion 14 of the container 10 respectively have a circular shape in a plan view. The flange portion 16 of the container 10 has a racetrack shape (shape formed by combining two semicircles and two straight lines) in a plan view. However, the shapes of the accommodating portion 12, the deformation portion 14, and the flange portion 16 are not limited. In the embodiment, the flange portion 16 is provided in the entire circumference of the accommodating portion 12. The entire circumference means that the entire circumference of the accommodating portion 12 is enclosed by the flange portion 16. The flange portion 16 is not necessarily provided in the entire circumference of the accommodating portion 12. Further, it is preferable that the flange portion 16 contains an adhesive on the surface to be brought into contact with the skin. The container 10 is attached to the skin because of the adhesive of the flange portion 16. Even in a case where the flange portion 16 does not contain an adhesive, the container 10 is attached to the skin because of an adhesive applied to the skin. Further, the container 10 is attached to the skin by attaching another member (medical tape) or the like onto the container 10.

As illustrated in FIG. 2, the accommodating portion 12 includes an inner space defined by an inner wall and an opening 12A. The opening 12A of the accommodating portion 12 is sealed by a lid 30. The accommodating portion 12 includes protrusions 12B which are arranged on the inner wall and protrude to the inner space. The accommodating portion 12 has a cylindrical shape according to the embodiment, but the shape of the accommodating portion 12 is not limited as long as the micro-needle array 40 can be accommodated.

The deformation portion 14 is disposed on a side opposite to the opening 12A and integrated with the accommodating portion 12. According to the embodiment, the deformation portion 14 has, for example, a convex shape with a vertex portion 14A separated from the micro-needle array 40. The vertex portion 14A of the deformation portion 14 indicates a portion furthest from the micro-needle array 40 in the deformation portion 14, and the convex shape means that the vertex portion 14A is not positioned in the inner space of the accommodating portion 12. The deformation portion 14 may have a plurality of vertex portions 14A. The deformation portion 14 being integrated with the accommodating portion 12 means that these are connected with each other. For example, in a case where the accommodating portion 12 is integrated with the deformation portion 14, the integration can be realized by separately forming the accommodating portion 12 and the deformation portion 14, fitting the accommodating portion 12 and the deformation portion 14 to each other, and then welding these. In the case where the accommodating portion 12 is integrated with the deformation portion 14, the integration can be made before or after the micro-needle array 40 is accommodated in the accommodating portion 12. In the case where the accommodating portion 12 is integrated with the deformation portion 14, the integration can be realized by integrally forming the accommodating portion 12 and the deformation portion 14. However, the integration method is not limited to these methods.

The deformation portion 14 can be formed in a cone shape. According to the embodiment, the deformation portion 14 has a conical shape. The deformation portion 14 may have an inner space, and the inner space of the deformation portion 14 can be formed to communicate with the inner space of the accommodating portion 12. The accommodating portion 12 has a structure in which the side opposite to the opening 12A is closed by the deformation portion 14. The type of the cone shape includes a conical shape, a pyramid shape, and a frustum shape.

The flange portion 16 is integrated with the accommodating portion 12 and brought into contact with the skin as described below. According to the embodiment, the flange portion 16 extends to the outside from the position of the opening 12A of the accommodating portion 12 and is bent to the side of the deformation portion 14 by the bent portion 18. According to the embodiment, the flange portion 16 is disposed at a position beyond the vertex portion 14A of the deformation portion 14 with respect to the opening 12A of the accommodating portion 12. The flange portion 16 is formed to be parallel to the sheet of the micro-needle array 40. The concept of parallel includes parallel and substantially parallel. As described below, the shape of the flange portion 16 is not particularly limited as long as the flange portion can be brought into contact with the skin. In a case where the accommodating portion 12 is integrated with the flange portion 16, the same method used for integration of the accommodating portion 12 with the deformation portion 14 can be applied.

Figure 3:
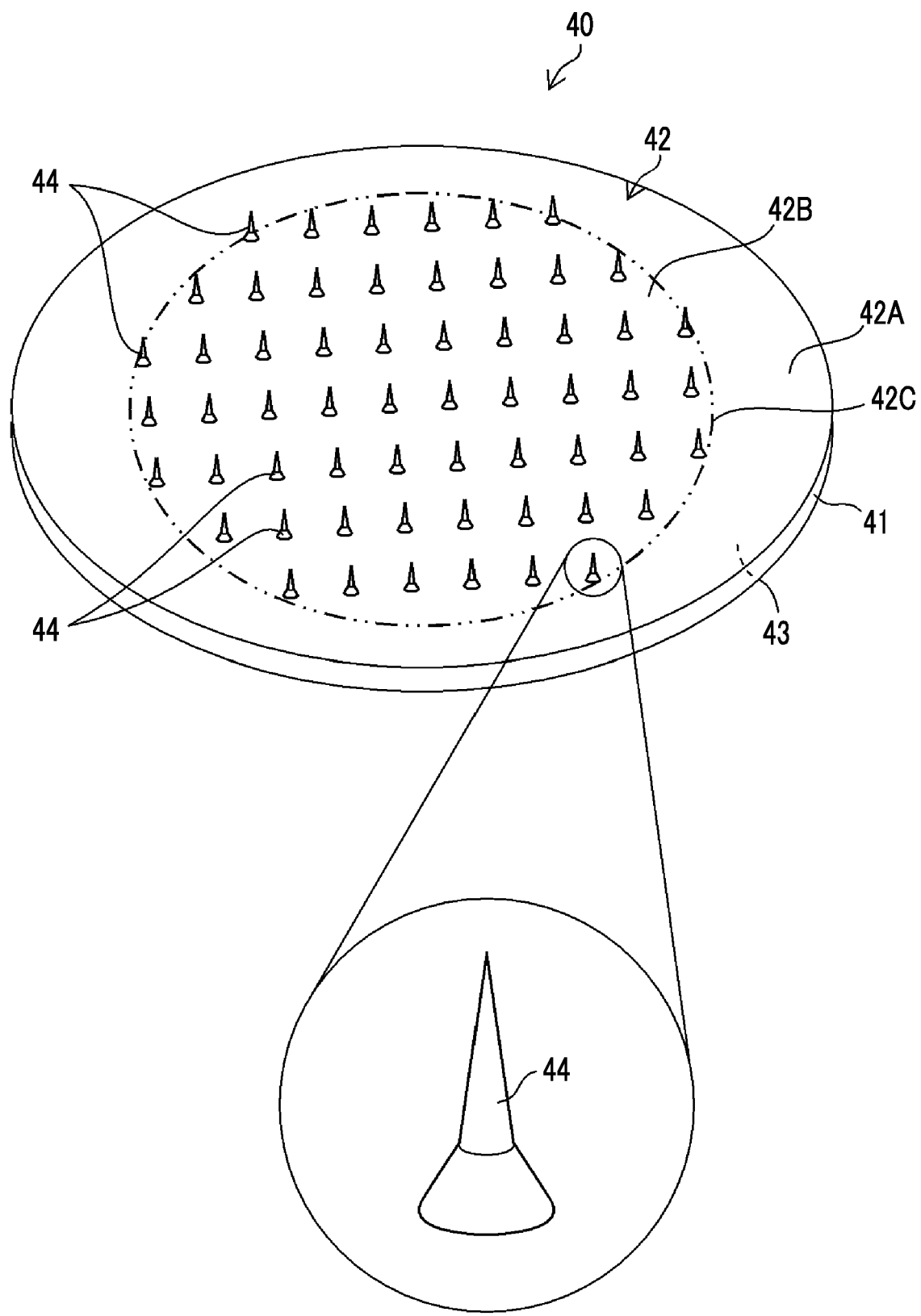
FIG. 3 is a perspective view illustrating a micro-needle array.

A typical structure of the micro-needle array 40 will be described with reference to FIG. 3. FIG. 3 is a perspective view illustrating the micro-needle array 40. As illustrated in FIG. 3, the micro-needle array 40 includes a circular sheet 41 having one surface 42 and the other surface 43 which face each other and a plurality of needles 44 arranged on the one surface 42 of the sheet 41. The needles 44 constitute micro-needles. The plurality of needles 44 are arranged in a micro-needle region 42B inside an outer peripheral surface 42A of the one surface 42. As illustrated in FIG. 3, the boundary between the outer peripheral surface 42A and the micro-needle region 42B is an imaginary line 42C that connects the needles 44, which are arranged on the outermost side of the micro-needle region 42B, from among the plurality of needles 44. According to the embodiment, an example in which the sheet 41 has a circular shape has been described, but the sheet 41 may have a rectangular shape.

The shape and the size of the sheet 41 or the needles 44 may be selected according to the applications of the micro-needle array 40. Further, the sheet 41 and the needles 44 may be formed of the same material or different materials. The micro-needle array 40 can be produced by integrally forming the sheet 41 and the needles 44, but the sheet 41 and the needles 44 may be formed separately.

The needles 44 respectively have a substantially cone shape, but may have a columnar shape or a frustum shape. According to the embodiment, the needles 44 are formed in order of a truncated cone portion and a cone from the one surface 42 toward the tip, but the shape thereof is not particularly limited as long as the needles can be punctured into the skin. It is preferable that the needles 44 are arranged in an array in a state of columns (lateral rows) and rows (vertical rows) at equal intervals.

Each needle 44 may be formed of a metal material, but it is preferable that each needle 44 is formed of a material that is dissolved after the needle 44 is punctured into the skin or the mucous membrane and then inserted into the body. Accordingly, as the material constituting the needles 44, a water-soluble polymer is preferable and polysaccharides are more preferable. As the material constituting the needles 44, it is preferable that the needles are formed of at least one material selected from the group consisting of hydroxyethyl starch, dextran, chondroitin sulfate, sodium hyaluronate, carboxymethyl cellulose, polyvinylpyrrolidone, polyoxyethylene polyoxypropylene glycol, and polyethylene glycol.

Each needle 44 is coated with or contains a medicine. Each needle 44 penetrates the skin and is punctured into the body when the sheet 41 is attached to the surface of the skin. In a case where the medicine is applied to each needle 44, the medicine is administered into the body from the surface of each needle 44. Further, in a case where the medicine is contained in each needle 44, since each needle 44 is formed of a material that is dissolved after each needle 44 is punctured into the body, the medicine in the needle 44 is administered into the body due to the dissolution of the needle 44 in the body.

The sheet 41 of the micro-needle array 40 has a diameter of 10 mm to 30 mm and a thickness of 0.1 mm to 5 mm. Further, each needle 44 has a length of 0.2 mm to 1.5 mm. Further, the number of needles 44 to be arranged on the one surface 42 of the sheet 41 is in a range of 4 to 1000. However, the values are not limited to these.

As illustrated in FIG. 2, the protrusions 12B support the outer peripheral surface 42A of the micro-needle array 40 in a state in which the tip of each needle 44 is directed to the gravity direction. The micro-needle array 40 is accommodated in the inner space of the accommodating portion 12 by the protrusions 12B in a state in which the needles 44 are directed to the opening 12A.

The other surface 43 of the micro-needle array 40 faces the deformation portion 14. According to the embodiment, the deformation portion 14 has a conical shape and the inner diameter of the deformation portion 14 decreases toward the vertex portion 14A. Even in a case where the container 10 is vibrated during the transport or the like, movement of the micro-needle array 40 is restricted by the protrusions 12B and the deformation portion 14. In the micro-needle array unit 1 of the embodiment, an adhesive for fixing the micro-needle array 40 is not disposed, but an adhesive may be disposed in the accommodating portion 12 to fix the micro-needle array 40.

Figure 4:
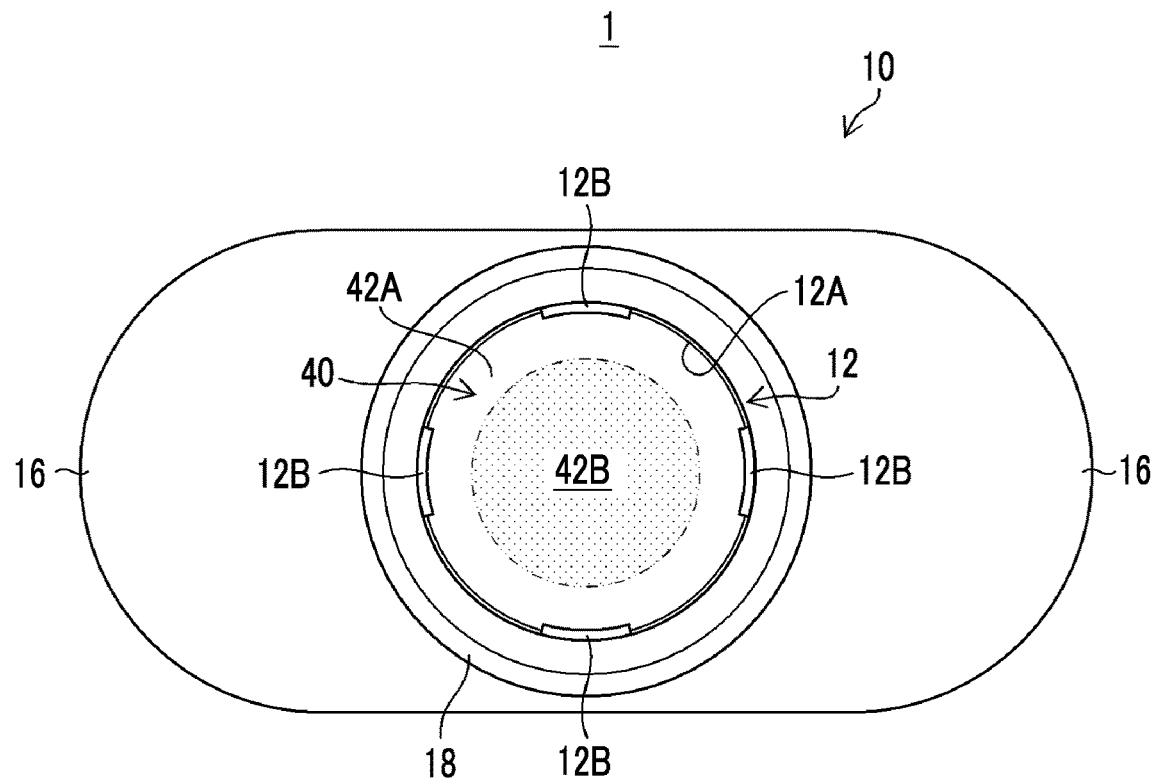
FIG. 4 is a bottom view illustrating the micro-needle array unit of FIG. 1.

FIG. 4 is a bottom view illustrating the micro-needle array unit 1. In the micro-needle array unit 1 of FIG. 4, the lid 30 is not illustrated for ease of understanding. FIG. 4 illustrates a state in which the micro-needle array 40 is exposed from the opening 12A. As illustrated in FIG. 4, four protrusions 12B are provided in the inner wall of the accommodating portion 12 at equal intervals. Four protrusions 12B support the outer peripheral surface 42A of the micro-needle array 40.

Figure 5:
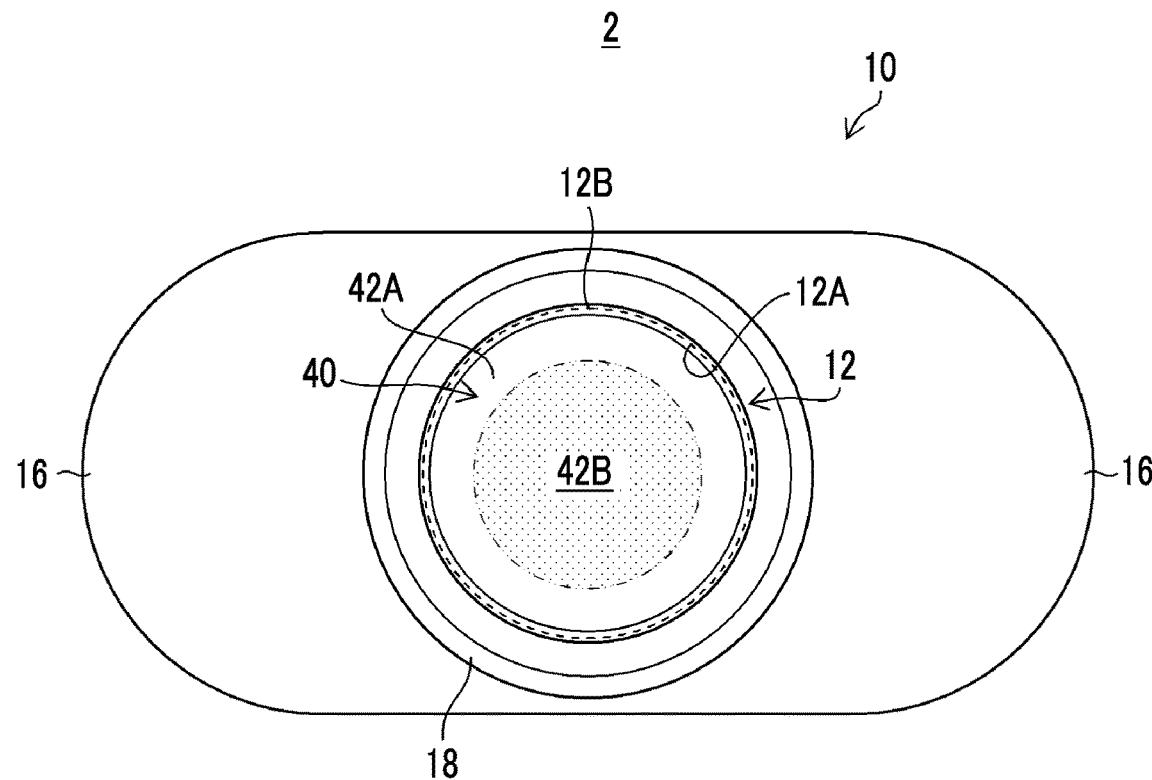
FIG. 5 is a bottom view illustrating another micro-needle array unit.

FIG. 5 is a bottom view illustrating a micro-needle array unit 2 in another form. In the micro-needle array unit 1 of FIG. 5, the lid 30 is not illustrated for ease of understanding. As illustrated in FIG. 5, the protrusions 12B are continuously provided along the inner wall of the accommodating portion 12. One protrusion 12B from among continuous protrusions supports the outer peripheral surface 42A of the micro-needle array 40.

The arrangement position and the number of protrusions 12B are not limited as long as the protrusions can support the outer peripheral surface 42A of the micro-needle array 40 in the state in which the tip of each needle 44 is directed to the gravity direction.

Next, a step of puncturing the micro-needle array 40 using the micro-needle array unit 1 will be described based on FIGS. 6 to 10. The constituent elements which are the same as those described in FIGS. 1 to 5 are denoted by the same reference numerals, and the description thereof will not be provided.

Figure 6:
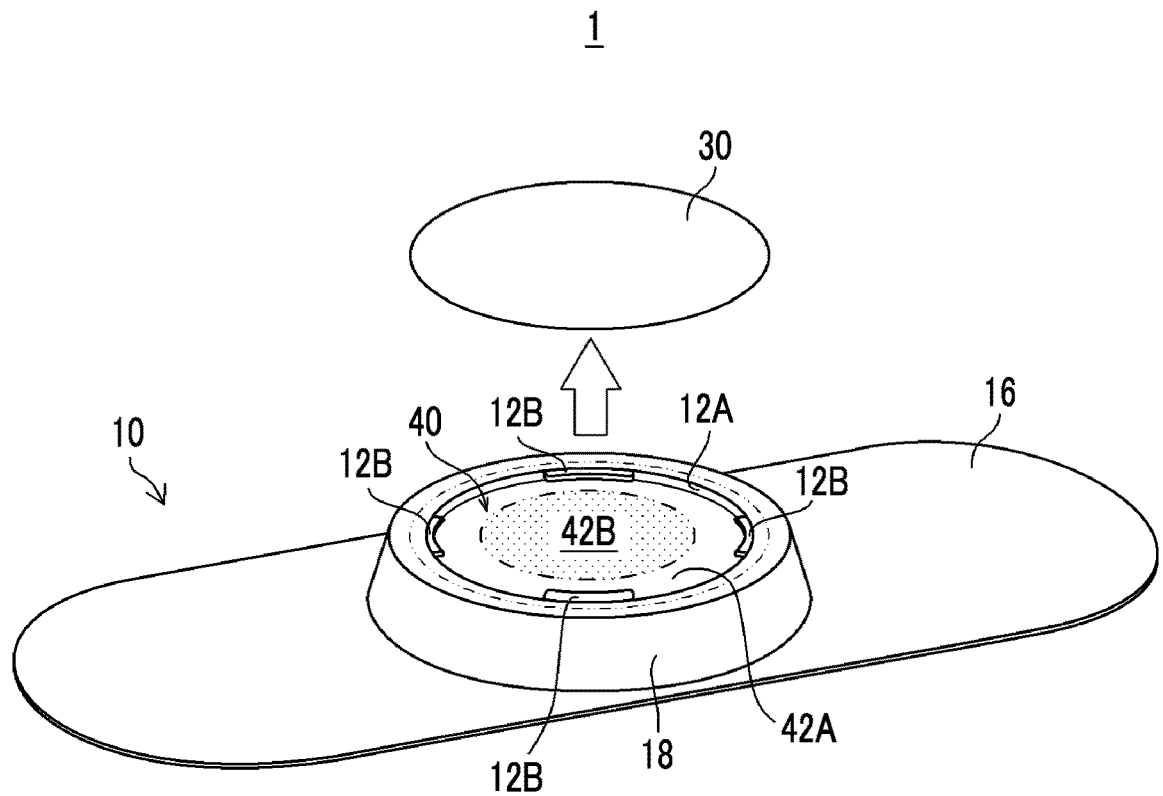
FIG. 6 is a perspective view of the micro-needle array unit illustrating a step of puncturing the micro-needle array.
Figure 7:
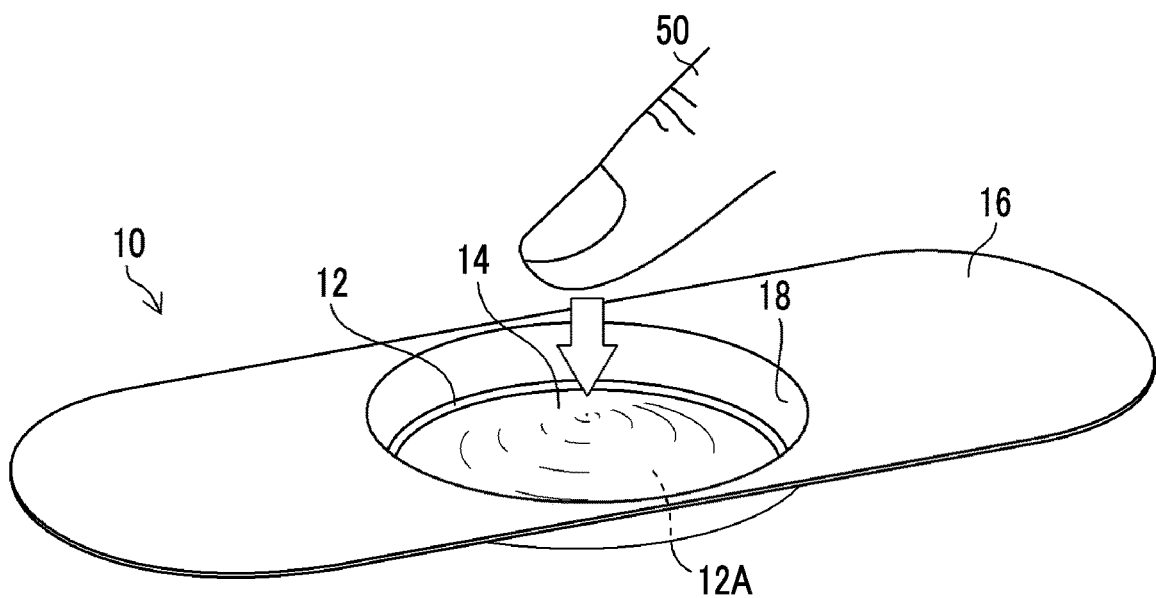
FIG. 7 is a perspective view of the micro-needle array unit illustrating the step of puncturing the micro-needle array.
Figure 8:
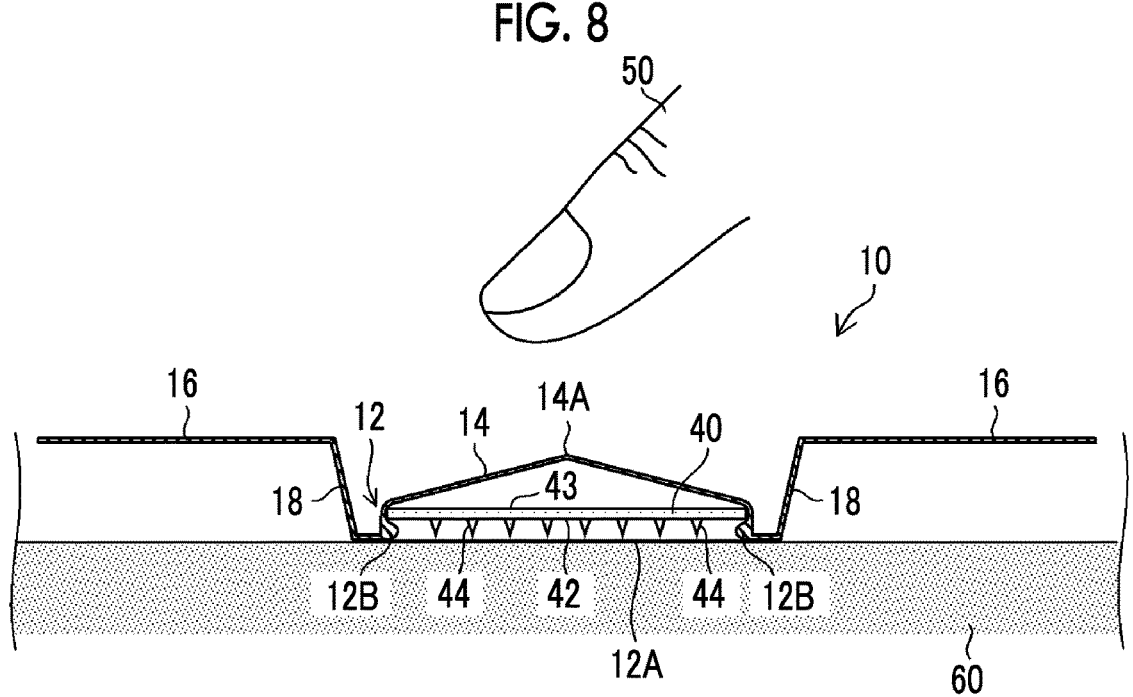
FIG. 8 is a cross-sectional view of the micro-needle array unit illustrating the step of puncturing the micro-needle array.
Figure 9:
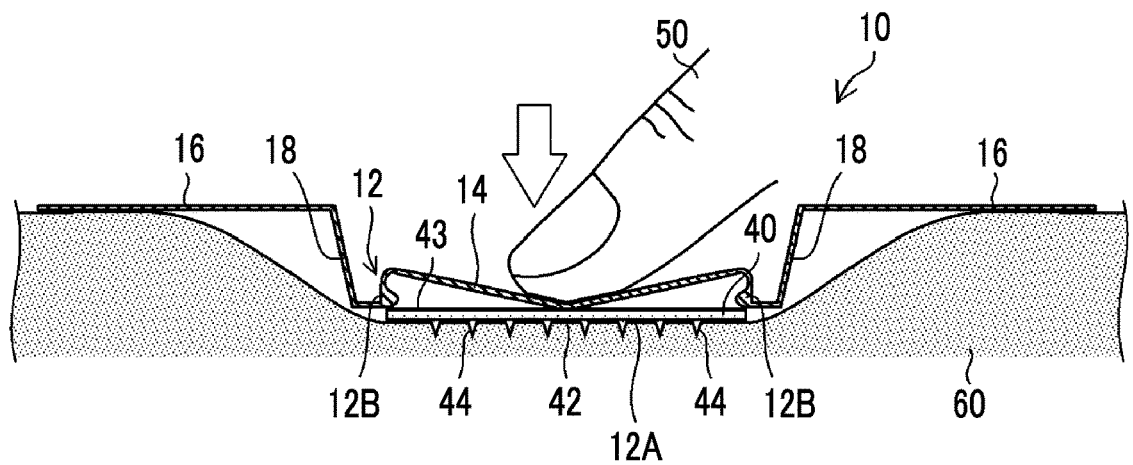
FIG. 9 is a cross-sectional view of the micro-needle array unit illustrating the step of puncturing the micro-needle array.
Figure 10:
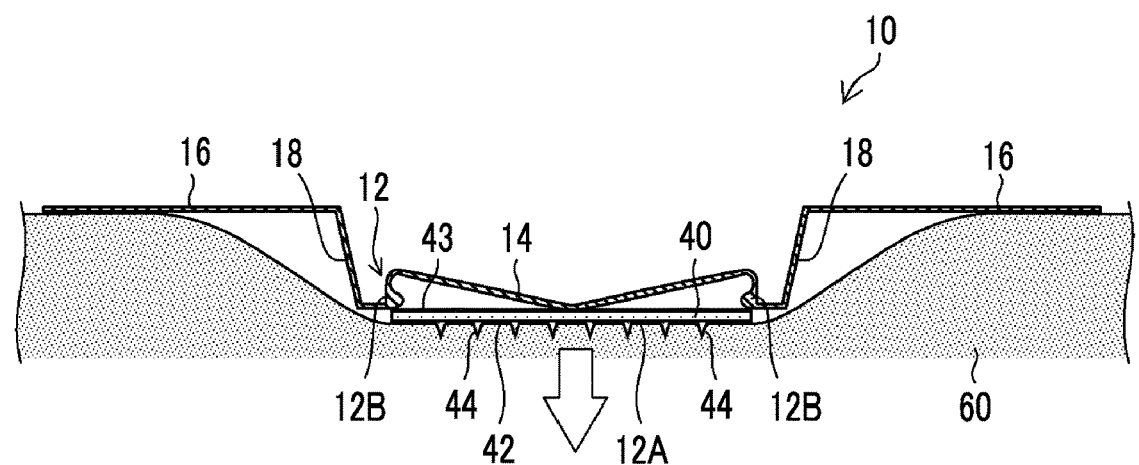
FIG. 10 is a cross-sectional view of the micro-needle array unit illustrating the step of puncturing the micro-needle array.

FIGS. 6 and 7 are perspective views of the micro-needle array unit illustrating a step of puncturing the micro-needle array 40. FIGS. 8 to 10 are cross-sectional views of the micro-needle array unit 1 illustrating the step of puncturing the micro-needle array 40.

As illustrated in FIG. 6, the lid 30 that seals the opening 12A of the accommodating portion 12 is peeled off from the container 10. The micro-needle region 42B of the micro-needle array 40 is exposed from the opening 12A. The lid 30 protects the needles 44 (not illustrated) of the micro-needle region 42B from being damaged until the micro-needle array unit 1 is used. It is preferable that the lid 30 has a knob portion in order to be easily peeled off.

As illustrated in FIG. 7, the container 10 is positioned on the skin. The opening 12A of the accommodating portion 12 is positioned toward the skin so that the needles 44 (not illustrated) of the micro-needle array 40 are directed to the skin. An external force in a direction of the opening 12A is applied to the deformation portion 14 using a finger 50.

FIG. 8 is a cross-sectional view of FIG. 7. As illustrated in FIG. 8, the container 10 is positioned on skin 60. A portion of the flange portion 16 protruding to the outside from the accommodating portion 12 is brought into contact with the skin 60. The finger 50 is positioned at a position separated from the vertex portion 14A of the deformation portion 14 in order to apply an external force to the deformation portion 14 in the direction of the opening 12A. The micro-needle array 40 is designated by the protrusions 12B and positioned in the inner space of the accommodating portion 12.

As illustrated in FIG. 9, the deformation portion 14 is pressed toward the skin 60 using the finger 50. The deformation portion 14 is deformed by receiving the external force in the direction of the opening 12A. The deformation portion 14 presses the other surface 43 of the micro-needle array 40. By pressing the other surface 43, the micro-needle array 40 passes through the protrusions 12B and are pushed out from the accommodating portion 12 to the outside. The micro-needle array 40 passes through the opening 12A and the needles 44 of the micro-needle array 40 are punctured into the skin 60. It is preferable that the protrusions 12B are elastically deformed during the passage of the micro-needle array 40. The insertion of the micro-needle array 40 into the accommodating portion 12 and the push-out of the micro-needle array 40 from the accommodating portion 12 can be smoothly carried out by the protrusions 12B to be elastically deformed.

Along with the application of the external force to the deformation portion 14, the skin 60 is moved until the flange portion 16 is brought into contact with the skin 60. In a case where the surface of the flange portion 16 which faces the skin 60 is provided with an adhesive, the flange portion 16 is attached to the skin 60.

As illustrated in FIG. 10, the deformation portion 14 is deformed by the external force. Even after the external force is removed, the deformation portion 14 maintains the deformed state. The deformed deformation portion 14 presses the micro-needle array 40 toward the skin 60.

Since the deformation portion 14 of the container 10 presses the micro-needle array 40 until the medicine of the micro-needle array 40 is administered after the puncture, detachment of the micro-needle array 40 from the skin 60 is prevented without the pressing of the finger 50.

According to the embodiment, since the flange portion 16 includes the bent portion 18, a step is formed between the puncture position of the micro-needle array 40 and the flange portion 16. Because of the step of the bent portion 18, the micro-needle array 40 is pushed down further than the skin 60 that comes into contact with the flange portion 16. By pushing the micro-needle array 40 down, a force of the skin 60 to return is increased so that a mutual pressing force between the skin 60 and the micro-needle array 40 is increased. Further, the needles 44 of the micro-needle array 40 enter a state of being easily punctured into the skin 60. It is preferable that the deformed deformation portion 14 is not deformed even in a case of receiving a pressure from the skin 60. The deformation portion 14 is capable of continuously pressing the micro-needle array 40.

According to the embodiment, the deformation portion 14 of the container 10 is disposed inside the projection plane of the accommodating portion 12, which accommodates the micro-needle array 40, in the center axis direction. Therefore, the disposition of the accommodating portion 12 and the deformation portion 14 in the container 10 leads to a decrease in size of the container 10. As the result, the size of the micro-needle array unit 1 (see FIG. 2) is decreased. Consequently, the micro-needle array 40 is easily punctured into the skin 60.

It is preferable that the container 10 and the lid 30 that constitute the micro-needle array unit 1 illustrated in FIG. 2 are formed of, for example, a polyethylene resin, a polypropylene resin, or a mixture of these. However, the materials are not limited to these. It is preferable that these materials respectively satisfy the "Specification of Plastic Container for Aqueous Injections (hereinafter, simply referred to as an injection container grade)". Further, the container 10 and the lid 30 may be formed of various resin materials satisfying the same specification other than those described above.

Among such materials, particularly a material that enables deformation of the shape of the deformation portion 14 and maintenance of the deformed shape when the deformation portion 14 receives the external force is selected. The material to be used is determined in consideration of the shape and the thickness of the deformation portion 14 and the magnitude of the external force required for the deformation.

Further, as illustrated in FIG. 2, it is preferable that each protrusion 12B is arranged closer to the side of the opening 12A than the side of the deformation portion 14. This means that, in a case where the distance from the opening 12A to the protrusion 12B and the distance from the position where the deformation portion 14 intersects with the accommodating portion 12 to the protrusion 12B are compared with each other, the distance from the opening 12A to the protrusion 12B is shorter than the other distance.

In a case where the protrusions 12B are provided on the side of the opening 12A, the needles 44 of the micro-needle array 40 become closer to the skin 60. In a case where the micro-needle array 40 passes through the protrusions 12B and is pushed out from the accommodating portion 12, the needles 44 are immediately punctured into the skin 60, and thus the micro-needle array 40 can be stably punctured into the skin 60.

Figure 11:
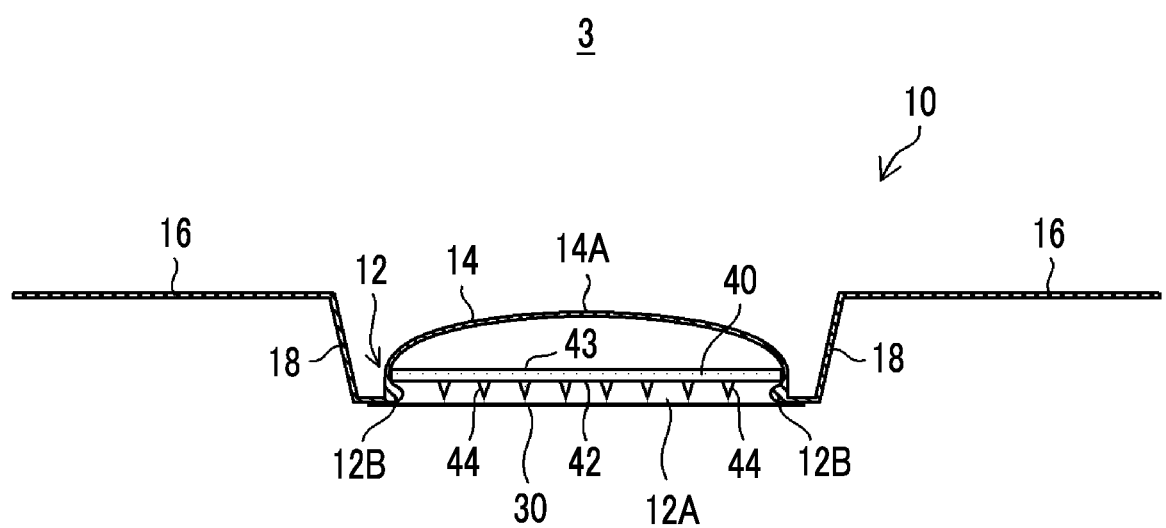
FIG. 11 is a cross-sectional view of a micro-needle array unit in another form.

FIG. 11 is a cross-sectional view illustrating a micro-needle array unit 3 in still another form. The constituent elements which are the same as those of the micro-needle array unit 1 are denoted by the same reference numerals, and the description thereof will not be provided.

A difference between the micro-needle array unit 3 and the micro-needle array unit 1 is the shape of the deformation portion 14.

In the micro-needle array unit 3, the deformation portion 14 has a convex shape with the vertex portion 14A and has a dome shape. The dome shape indicates a shape having a curved surface with a certain curvature radius and examples thereof include a hemispherical shape. However, the example is not limited to the hemispherical shape and the curvature radii are not necessarily the same in the entirety of the shape.

The micro-needle array unit 3 which includes the deformation portion 14 in the dome shape can exert the same effects as those of the micro-needle array unit 1.

Figure 12:
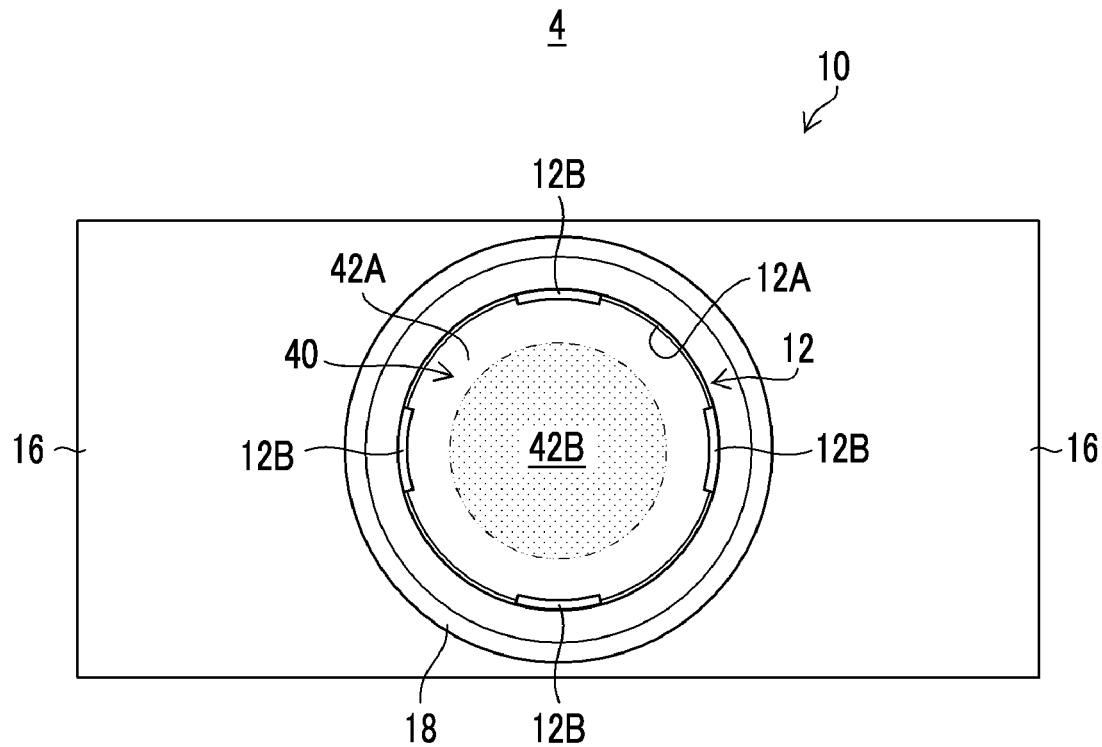
FIG. 12 illustrates bottom views of micro-needle array units in still another form.
Figure 12:
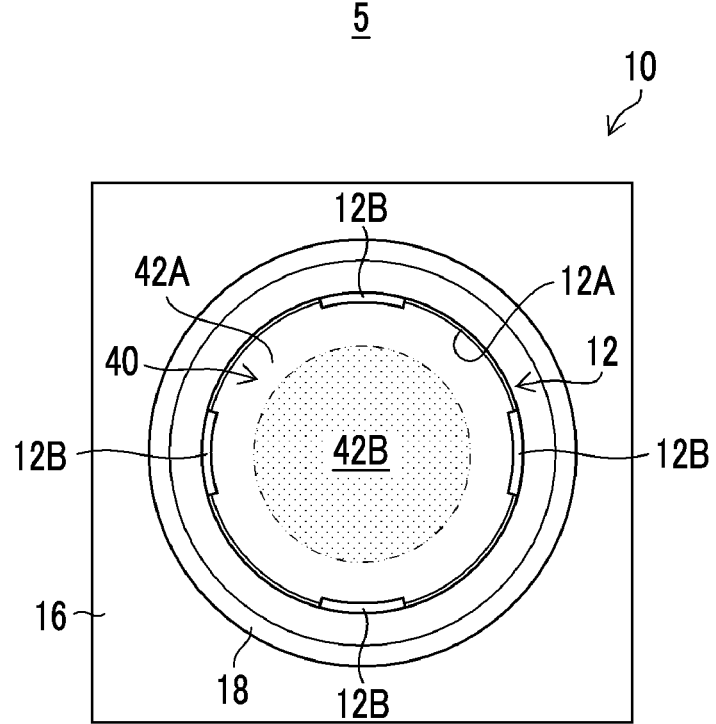
Figure 13:
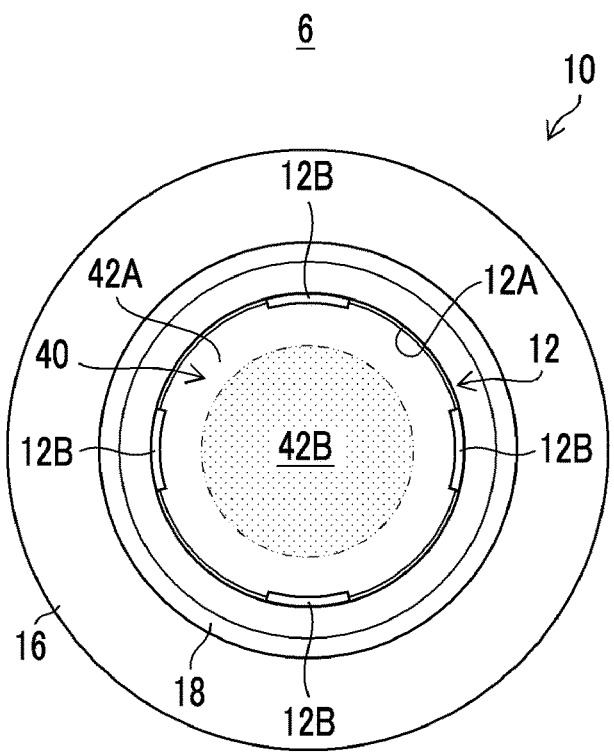
FIG. 13 illustrates bottom views of micro-needle array units in still another form.
Figure 13:
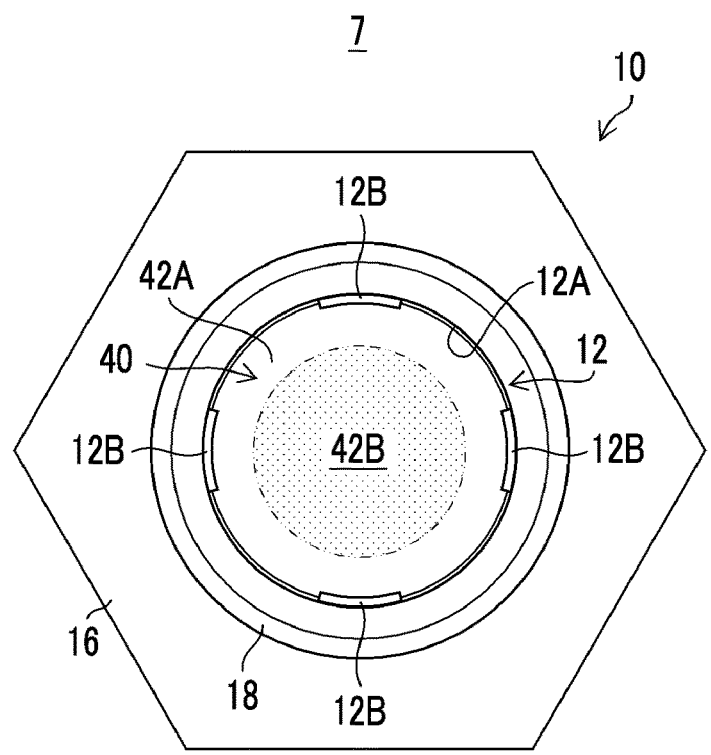

FIG. 12 illustrates bottom views of micro-needle array units 4 and 5 in still another form, and FIG. 13 illustrates bottom views of micro-needle array units 6 and 7 in still another form.

The constituent elements which are the same as those of the micro-needle array unit 1 are denoted by the same reference numerals, and the description thereof will not be provided.

As illustrated in FIG. 12, a difference between the micro-needle array unit 4 and the micro-needle array unit 1 is the shape of the flange portion 16. The micro-needle array unit 4 has a rectangular shape. Further, a difference between the micro-needle array unit 5 and the micro-needle array unit 1 is the shape of the flange portion 16. The micro-needle array unit 5 has a square shape.

As illustrated in FIG. 13, a difference between the micro-needle array unit 6 and the micro-needle array unit 1 is the shape of the flange portion 16. The micro-needle array unit 6 has a circular shape. Further, a difference between the micro-needle array unit 7 and the micro-needle array unit 1 is the shape of the flange portion 16. The micro-needle array unit 7 has a polygonal shape, which is a hexagon.

The micro-needle array units 4, 5, 6, and 7 having the flange portions 16 in shapes different from one another can exert the same effects as those of the micro-needle array unit 1. The lid 30 is not illustrated in FIGS. 12 and 13.

Basically, the flange portions 16 are attached to the skin. In a case where the shapes of the flange portions 16 are different from one another, this means that the areas where the flange portions 16 are in contact with the skin are different from one another.

It is preferable to select the container 10 that includes the flange portion 16 with an appropriate shape in consideration of the location where the micro-needle array 40 is punctured or the like.

Further, FIG. 12 and FIG. 13 illustrate a plurality of flange portions 16 having shapes different from one another, but the shapes are not limited to these.

Figure 14:
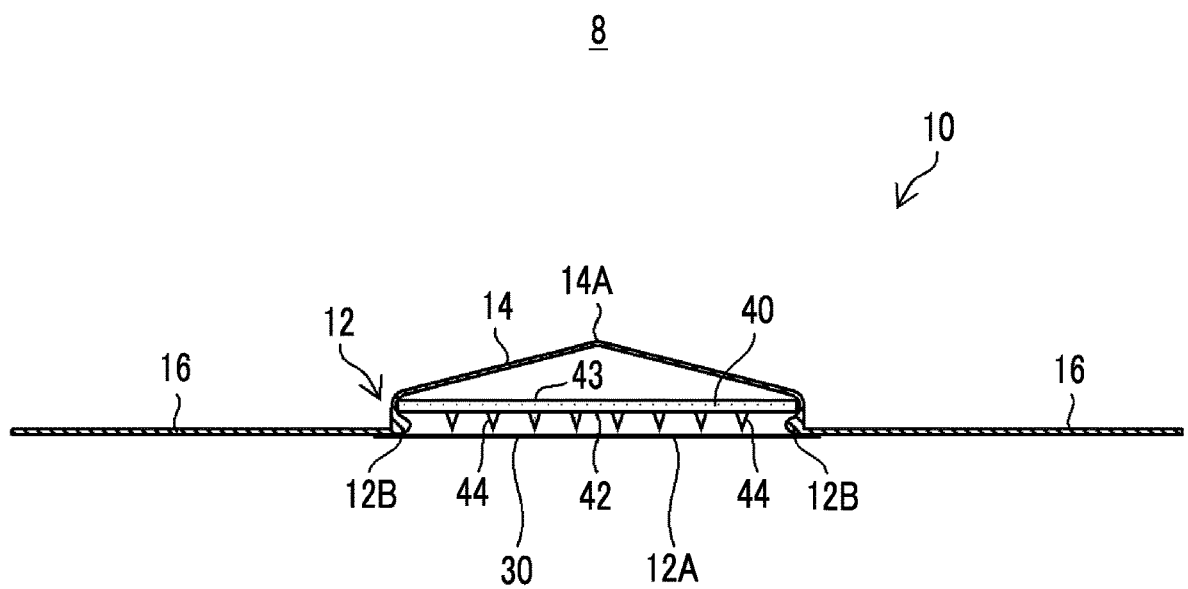
FIG. 14 is a cross-sectional view of a micro-needle array unit in still another form.

FIG. 14 is a cross-sectional view illustrating a micro-needle array unit 8 in still another form. As illustrated in FIG. 14, a difference between the micro-needle array unit 8 and the micro-needle array unit 1 is the shape of the flange portion 16. In the container 10 of the micro-needle array unit 8, the flange portion 16 does not include a bent portion. The flange portion 16 extends to the outside from the position of the opening 12A of the accommodating portion 12. The flange portion 16 is formed to be parallel to the sheet of the micro-needle array 40. The concept of parallel includes parallel and substantially parallel. The micro-needle array unit 8 is capable of further reducing the pressure between the micro-needle array 40 and the skin than the micro-needle array unit having a bent portion.

The micro-needle array unit 8 having the flange portion 16 in a different shape can exert the same effects as those of the micro-needle array unit 1.

Figure 15:
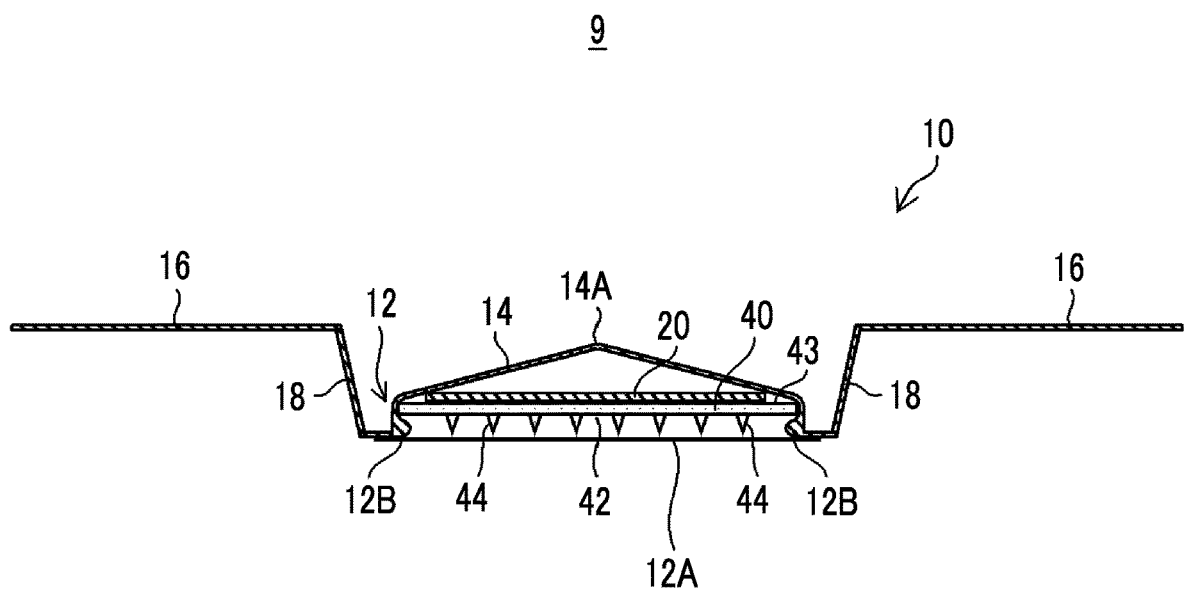
FIG. 15 is a cross-sectional view of a micro-needle array unit in still another form.

FIG. 15 is a cross-sectional view illustrating a micro-needle array unit 9 in still another form. As illustrated in FIG. 15, the micro-needle array unit 9 is different from the micro-needle array unit 1 in terms that the micro-needle array unit 9 includes a flat plate 20 on a side of the other surface 43 of the micro-needle array 40. The flat plate 20 and the container 10 may be separate members or may be integrated with each other.

The deformation portion 14 is deformed due to the external force and the deformed deformation portion 14 presses the micro-needle array 40 into the skin (not illustrated) through the flat plate 20. The entire surface of the micro-needle array 40 can be uniformly pressed by the flat plate 20. The micro-needle array unit 9 can exert the same effects as those of the micro-needle array unit 1.

The embodiments which have been described and are illustrated in the drawings are merely examples and can be modified without departing from the gist and the scope of the present invention.

EXPLANATION OF REFERENCES

1: micro-needle array unit
2: micro-needle array unit
3: micro-needle array unit
4: micro-needle array unit
5: micro-needle array unit
6: micro-needle array unit
7: micro-needle array unit
8: micro-needle array unit
9: micro-needle array unit
10: container
12: accommodating portion
12A: opening
12B: protrusion
14: deformation portion
14A: vertex portion
16: flange portion
18: bent portion
20: flat plate
30: lid
40: micro-needle array
41: sheet
42: one surface
42A: outer peripheral surface
42B: micro-needle region
42C: imaginary line
43: the other surface
44: needle
50: finger
60: skin

What is claimed is:

1. A micro-needle array unit comprising:
a micro-needle array which includes a sheet and a plurality of needles arranged inside an outer peripheral surface of one surface of the sheet;
a container which accommodates the micro-needle array and includes an accommodating portion having an opening and a protrusion that supports the outer peripheral surface of the micro-needle array, a deformation portion disposed on a back side of the micro-needle array opposite to the opening and integrated with the accommodating portion, and a flange portion integrated with the accommodating portion and brought into contact with the skin; and
a lid which seals the opening of the container,
wherein the deformation portion is configured to be depressed to press a back surface of the micro-needle array due to an external force being applied in a direction of the opening, and
the micro-needle array passes through the protrusion and is pushed to the outside from the accommodating portion by the pressing of the back surface of the micro-needle array.

2. The micro-needle array unit according to claim 1, wherein the protrusion is arranged closer to a side of the opening than a side of the deformation portion.

3. The micro-needle array unit according to claim 1, wherein the deformation portion has a convex shape with a vertex portion separated from the micro-needle array.

4. The micro-needle array unit according to claim 3, wherein the convex shape is a dome shape or a cone shape.

5. The micro-needle array unit according to claim 1, wherein the protrusion comprises a plurality of protrusions, and the plurality of protrusions are arranged at equal intervals in the accommodating portion.

6. The micro-needle array unit according to claim 1, wherein the protrusion comprises a plurality of protrusions, and the plurality of protrusions are continuously arranged in the accommodating portion.

7. The micro-needle array unit according to claim 1, wherein the flange portion includes an adhesive on a side in contact with the skin.

8. The micro-needle array unit according to claim 1, further comprising:
a flat plate on a side of the other surface of the micro-needle array.

9. The micro-needle array unit according to claim 1, wherein the flange portion is provided in the entire circumference of the accommodating portion.

10. The micro-needle array unit according to claim 1, wherein the flange portion includes a bent portion which is bent to the side of the deformation portion.

11. The micro-needle array unit according to claim 10, wherein the bent flange portion is disposed at a position beyond the deformation portion with respect to the opening of the accommodating portion.

12. A container which accommodates a micro-needle array including a sheet and a plurality of needles arranged inside an outer peripheral surface of one surface of the sheet, the container comprising:
an accommodating portion which includes an opening and a protrusion that supports the outer peripheral surface by directing the needles to the opening;
a deformation portion which is disposed on a back side of the micro-needle array opposite to the opening and integrated with the accommodating portion; and
a flange portion integrated with the accommodating portion and brought into contact with the skin,
wherein the deformation portion is configured to be depressed to press a back surface of the micro-needle array due to an external force being applied in a direction of the opening, and
the micro-needle array is pushed out from the accommodating portion by the pressing of the back surface of the micro-needle array.

* * * * *